(12) United States Patent
Hu (10) Patent No.: US 6,974,805 B2
(45) Date of Patent: Dec. 13, 2005

(54) CONFIGURATION OF GLYCOSAMINOGLYCANS

(76) Inventor: Min Hu, 4483 Macbeth Cir., Fremont, CA (US) 94555

( * ) Notice: Subject to any disclaimer, the term of this patent is extended or adjusted under 35 U.S.C. 154(b) by 0 days.

(21) Appl. No.: 10/632,599

(22) Filed: Aug. 1, 2003

(65) Prior Publication Data

US 2004/0058858 A1 Mar. 25, 2004

Related U.S. Application Data

(60) Provisional application No. 60/400,078, filed on Aug. 1, 2002.

(51) Int. Cl.[7] .................. A61K 31/726; A61K 31/715; A61K 31/738
(52) U.S. Cl. ......................... 514/54; 536/55.1; 536/53
(58) Field of Search .......................... 514/54; 536/55.1, 536/53

(56) References Cited

U.S. PATENT DOCUMENTS 5,510,328 A * 4/1996 Polarek et al. ................. 514/8
5,766,631 A * 6/1998 Arnold ......................... 424/486

* cited by examiner

*Primary Examiner*—James O. Wilson
*Assistant Examiner*—Michael C. Henry
(74) *Attorney, Agent, or Firm*—Bo-In Lin (57) ABSTRACT

The present invention provides stable glycosaminoglycan (GSG) structures and methods of use of such GAG structures. These structures comprise a core of free GAG, a coating of crosslinked GAG surrounding the core, and a layer of a positively charged moiety surrounding the crosslinked GAG layer. These GAG structures provide improved stability, both in in vivo and external use. Furthermore, resurfacing of the structures provides improved cell adhesion and thus improved delivery of the GAG into living cells and tissues.

2 Claims, 8 Drawing Sheets

TABLE 1: Adhesion and Proliferation of Fibroblasts on HyA Strands Resurfaced With One of Four Different Amino Acids or Polypeptides

| Resurfacing Treatment | Cell Attachment Count Proliferation (Average # per 1 mm HyA Strand) | Proliferation |
|---|---|---|
| None | 0-2 | − |
| Poly-D-lysine | 50-100* | + + |
| Poly-L-lysine | 40-80* | + + |
| Glycine | 0-7 | + |
| L-glutamine | 0-5 | + |

*$p < 0.01$.

TABLE 3. Scar areas of incision wounds

Figure 4A. The HyA strand stained with Alcian Blue.

Figure 4B. The outside layer of the strand was broken.

Figure 4C. The cells grow on the HyA strand.

CONFIGURATION OF GLYCOSAMINOGLYCANS

This Application is a Formal Application and claim a Priority Date of Aug. 1, 2002 benefited from a Provisional Patent Application 60/400,078 filed by the same inventor of this Patent Application.

FIELD OF THE INVENTION

The present invention relates generally to structures composed of glycosaminoglycans with or without living cells, methods of producing glycosaminoglycan structures, and methods of treating subjects using these structures.

BACKGROUND OF THE INVENTION

Slow healing or lack of healing of dermal wounds (e.g., decubitus ulcers, severe burns and diabetic ulcers) and eye lesions (e.g., dry eye and corneal ulcers), is a serious medical problem, affecting millions of individuals and causing severe pain or death in many patients. Healing of surgical wounds can also be slow or otherwise problematic, particularly in aging and diabetic individuals. Although wounds may be quite dissimilar in terms of cause, morphology and tissue affected, they share a common healing mechanism. Each repair process ultimately requires that the correct type of cell migrate into the wound in sufficient numbers to have an effect: macrophages to debride wounds, fibroblasts for the formation of new collagen and other extracellular matrix (ECM) components in wounds where the extracellular matrix was damaged, capillary endothelial cells to provide the blood supply, and epithelial cells to ultimately cover the wounds.

However, under certain circumstances, such as burn wounds, and hereto lacking of sufficient living skin to support the regeneration of the wound, and then the wounds will last longer and have chances to develop severe infection that some time causes the loss of the lives. Hence resulted hypertrophic burn scars are notoriously difficult to treat because of their extensive tissue involvement.

The standard method for grafting extensive or deep burn wounds used full-thickness sheet grafts or narrowly meshed, thick, split-thickness skin grafts [Lattari,et al. J Burn Care Rehabil 18:147–155 (1997)]. This method, however, creates an additional complication-prone wound at the donor site. Donor sites can be painful and may develop infection, hypertrophic scarring, blistering, and hyper- or hypopigmentation. The problem of donor site scar hapertrophy occurs most frequently when a graft is taken at more than 0.012 inch thick, leaving a residual dermal bed that is too thin. Meanwhile, early and permanent coverage of extensive burn wounds is still difficult because of the shortage of the donor sites.

The unwounded dermis owes much of its structure and strength to the interactions of cells with the ECM. It is well understood now that migration of fibroblasts and keratinocytes plays an important role in wound healing. The ECM is the key dynamic assemblage of interacting molecules that regulate cell functions and interactions in response to stimulation of wounds. This matrix includes several proteins known to support the attachment of a wide variety of cells, including fibronectin, vitronectin, thrombospondin, collagens, and laminin. Although fibronectin is found at relatively low concentrations in unwounded skin, plasma fibronectin deposition occurs soon after wounding. When tissue is damaged, the ECM must be replaced to provide a scaffold to support cell attachment and migration. In addition to providing a scaffold, extracellular matrices can also direct cellular proliferation and differentiation. An extracellular matrix can, therefore, direct healing of a tissue in such a way that the correct tissue geometry is restored.

Acceleration of the healing process can be greatly aided by a better understanding of the factors that influence the synthesis of granulation tissue, which fills the wound before epithelialization. An important phase of early wound healing involves fibroblast secretion of glycosaminoglycans (GAGs), which form a hydrophilic matrix suitable for remodeling during healing. Tissue-engineering techniques generally focus on mimicking the ECM by creating a scaffolding of resorbable materials that serves to promote wound healing. However, the use of GAGs in such materials is hindered by the instability of free GAGs.

Modification of GAGs, such as hyaluronan, in order to provide more stable structures has been an area of interest in this field. For example, U.S. Pat. No. 4,851,521 describes esters of hyaluronic acid in which all or only a portion of the carboxylic groups of the acid are esterified. See also Kuo J W et al., *Bioconjugate Chem* 2:232–241(1991). These GAG modifications however, alter the biological activity of the GAGs and renders them less effective than their free counterparts. In addition, structures formed with these esterified GAGs are instable when in contact with liquid, such as body fluids, and thus structures composed of these molecules do not retain their integrity following application to a subject.

There is a need in the art for compositions, devices and methods for providing site-specific GAG administration, and in particular for GAG structures that are stable and cell or tissue accessible in vivo and which provide bioavailable GAG.

SUMMARY OF THE INVENTION

The present invention provides stable glycosaminoglycan (GSG) structures and methods of use of such GAG structures. These structures comprise a core of free GAG, a coating of crosslinked GAG surrounding the core, and a layer of a positively charged moiety surrounding the crosslinked GAG layer. These GAG structures provide improved stability, both in in vivo an external use. Furthermore, resurfacing of the structures provides improved cell adhesion and thus improved delivery of the GAG into cells, tissues and/or organs.

In one aspect of the invention, methods are provided for preparing compounds having of a core of free GAG, a surrounding layer of cross-linked GAG, and a layer of a positively charged moiety. The method comprises the steps of cross-linking an outer layer of a GAG substrate solution (premade into a structure of any shape) with a high concentration (e.g., between about 35% to 85%) of a cross-linker, which effectively crosslinks the GAGs on the periphery of the substrate while leaving the GAGs in the core of the substrate free, ie., not crosslinked. The GAG structures can be formed into a desired shape prior to cross-linking, and the crosslinkers help to fix and stabilize the structures in the particular shape. Preferably, the cross-linking reagent is an aldehyde, e.g., glutaraldehyde, formaldehyde and the like. GAG structures formed according to the invention, are particularly advantageous in that they do not dissolve upon contact with bodily fluids and provide cells access to bioavailable, free GAG. Also, as any excess crosslinking agent can be removed from the structures without affecting the structural integrity, these structures are non-toxic upon administration.

A particular embodiment of the invention provides a composition comprising the GAG structures of the invention and an appropriate excipient. The excipient may be any acceptable carrier of the GAG structures of the invention, including water.

It is thus an object of the present invention to provide a polymeric composition that can provide for directed release of GAGs and can serve as a substrate for cell growth.

In a particular embodiment of the present invention, the GAG structures are used in or on devices and/or compositions that promote wound healing." The GAG structure can provide bioactive GAG in a controlled manner, e.g., by application externally to a dermal wound, or internally to a damaged organ or an incised vein or artery with or without living cells. The GAG structure can be cultured with various cells prior to use, e.g., hyaluronan (HyA) structures can be cultured with keratinocytes or fibroblasts for use in a liquid bandage.

In one aspect of the invention, the GAG is introduced to a wound site using a delivery vehicle such as a solid wound dressing, a liquid bandage, an adhesive and the like, which delivery vehicles comprises the GAG structures of the invention.

It is thus an object of the present invention to provide drug delivery devices, particularly wound dressings, comprising such polymeric delivery vehicles for release of wound-healing agents to aid in the wound healing process.

In another embodiment of the invention, the GAG structures are provided to modulate other GAG-mediated events, e.g., resurfaced GAG structures may be introduced into the synovial fluid of a joint to alleviate arthritis.

It is thus an object of the present invention to provide methods of treatment for GAG-mediated physiological conditions and/or disease.

An advantage of the present invention is that the cross-linking agent is removed from the delivery device, thus limiting potential toxicity from the cross-liking agents.

It is another advantage of the present invention that the GAG structures are stable in vivo for up to 6 months.

It is yet another advantage that the GAG structures of the invention provide enhanced cell attachment. These and other objects of the invention will be apparent from the following description and appended claims, and from practice of the invention.

These and other objects, advantages, and features of the invention will become apparent to those persons skilled in the art upon reading the details of the invention as more fully described below.

BRIEF DESCRIPTION OF THE DRAWINGS

Table 1 is a graph illustrating the structural stability of HyA structures crosslinked with 25% (circles) and 50% (triangles) concentrations of glutaraldehyde for different time periods.

Table 2 is a graph illustrating the wound closure time for the experimental rats with HyA treated wounds and control groups that the wounds were not treated by HyA grafts but a saline wash.

Table 3 is a graph indicating the comparison of the scar areas of the different groups. The data were collected by the measurement of the exact area on the tissue' histologic stained slides by Confocol microscopy.

DETAILED DESCRIPTION OF INVENTION

Before the present methods and compositions are described, it is to be understood that this invention is not limited to particular methods and compositions described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either-or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a glycosaminoglycan" includes a plurality of such glycosaminoglycan molecules and reference to "the cross-linking agent" includes reference to one or more cross-linking agent and equivalents thereof known to those skilled in the art, and so forth. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "glycosaminoglycan" and "GAG", as used interchangeably herein, refer to a macromolecule comprised of carbohydrate. The GAGs for use in the present invention may vary in size and be either sulfated or non-sulfated. The GAGs which may be used in the methods of the invention include, but are not limited to, hyaluronic acid, chondroitin sulfates (e.g., neurocan and brevican), laminin, keratin sulfate, chitin and heparin. The term as used herein is intended to encompass modified GAGs (e.g., sulphated GAGs, and GAGs complex with heavy metal ions such as $Cu^{2+}$ and $Zn^{2+}$) as well as naturally occurring forms.

The terms "free glycosaminoglycan" and "free GAG" as used interchangeably herein refer to GAGs that are not chemically cross-linked or substantially chemically cross-linked. Free GAGs are preferably available in a naturally occurring form, including but not limited to a monomer or a dimer. The term is also intended to encompass GAGs that are modified to be in a more active form and accessible to the appropriate cells. As used herein, this term generally describes the bioavailable GAG molecules present in the core of the GAG structures. The core of the GAG structures of the invention comprise at least 50% free GAG, more preferably about 75% free GAG, and even more preferably at least 90% free GAG. Specific terms such as "free HyA" and "free heparin" refer to a free form of that particular GAG.

The term "glycosaminoglycan structure", "GAG structure", "cross-linked GAG structure" and the like as used herein refer to a structure having an external coating of crosslinked GAG and an internal core of free GAG. These structures may or may not have an additional coating of a positively charged molecule, e.g., polylysine. Specific terms such as "HyA structure" refer to a GAG structure composed of the particular GAG. The "GAG structure" may optionally be resurfaced.

The term "glycosaminoglycan substrate", "GAG substrate" and the like as used interchangeably herein refers to a free glycosaminoglycan preparation that is exposed to the cross linking agent to produce the glycosaminoglycan structure. The GAG substrate may be a dried preparation of GAG, or it may be in a liquid form upon exposure to the cross linking agent. The "GAG substrate" may optionally be resurfaced.

The term "resurfaced GAG structure" as used herein refers to a GAG structure with an external coating of a charged molecule. Preferably the charged molecule is a suitable polymer with constituent primary amine groups, including polyvinylamines, polyacrylamides, and polyamino acids, such as polyaspartic acid, polyglutamic acid, and preferably polylysine.

The term "isolated" means the substance of interest is removed from its natural surroundings. However, some of the components found with it may continue to be with an "isolated" protein. Thus, an "isolated GAG" is not as it appears in nature but may be substantially less than 100% pure GAG (for example, but not limited to, 50%, 85%, or 90–95% pure.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for disease and/or adverse effect attributable to the disease. In one embodiment, "treatment" as used herein covers any treatment of a disease in a mammal, particularly a human, and includes: (a) preventing the condition from occurring in a subject which may be predisposed to the disease but has not yet been diagnosed as having it; (b) inhibiting the condition, i.e., arresting its development; or (c) relieving the condition, i.e., causing regression of the disease. The present invention is especially pertinent to the treatment of a wound, for which the GAG treatment can be used to facilitate healing. The present invention also pertains to treatments in which delivery of a GAG to a specific site will treat a disease, such as delivery of GAG to synovial fluid to treat arthritis.

GENERAL ASPECTS OF THE INVENTION

The present invention is based in part on the surprising finding that use of a high concentration of a cross-linking agent, such as glutaraldehyde, resulted in the cross linking of the GAG molecules on the edge of the treated structure, but not in the core. This results in a structure having an outer coating of crosslinked GAG, and an inner core of free, bioactive GAG. The invention provides a composition that has the ability to maintain its structural integrity upon contact with a liquid (e.g., a body fluid) due to the cross-linked outer coating, and yet maintain the bioavailability of the GAG by providing free GAG in the core. The free GAG in the cores of such structures is accessible to cells exposed to these structures, as the outer cross-linked coating does not impede the ability of a cell (e.g., a fibroblast) to send outgrowths into the free core. In addition, by resurfacing the structure, e.g., by adding a charged outer coating to the GAG structure, providing for better adherence of cells to the GAG structures and for delivery of free GAG to cells.

Central to the present invention is the high concentration of the cross-linking agent. The cross-linking agent must be of a sufficient concentration to allow cross-linkage of the outer layer of the GAG without substantially crosslinking the internal GAG. Preferably the crosslinking agent is provided in at least a 35% to 99% solution, more preferably in a 40% to 85% solution, and even more preferably in a 50%–75% solution. The cross-linker used to prepare the structures of the invention can be any agent with the ability to cross-link either a single GAG to itself, e.g., HyA-HyA crosslinking, or to crosslink different GAGs to one another, e.g., HyA-Heparin crosslinking. Exemplary cross-linking agents that may be used in the methods of the invention include, but are not limited to: glutaraldehyde, formaldehyde, vinyl sulphone, biscarbodiimides, carbodiimides, an appropriate alcohol series or ultraviolet light.

The GAG substrate should be exposed to the crosslinking agent for a period of time sufficient to provide enhancing stability of the GAG structure. For example, when glutaraldehyde is used as the crosslinking agent, an incubation period of 72 hours was found to provide good crosslinking of the GAG structures. Other cross linking agents will have different desirable incubation times, as will be apparent to one skilled in the art upon reading this disclosure. Following this incubation period, excess cross-linking agent is optionally washed from the structure.

The present invention is suitable for creating structures comprising any GAG, including those currently known and those that are as yet unidentified. The structures can be formed from a single GAG, such as a structure containing hyaluronic acid, or can comprise two or more GAGs, such as a structure containing hyaluronic acid and heparin. The structures preferably are formed by cross linking hyaluronic acid, the chondroitin sulfates (e.g., netirocan and brevican), keratan sulfate, chitin and/or heparin.

Following cross-linking of the outer layer of the GAGs, a layer of a positively charged coating is added to the GAG structure to resurface the structure. Suitable moieties include, but are not limited to, polyvinylamines, polyacrylamides, and polyamino acids, such as polyaspartic acid, polyglutamic acid, and preferably polylysine. In addition, other molecules can be used and the structure subjected to cation exchange to add a positive charge to the surface of the GAG structure. The positively charged molecules are then crosslinked to the outer layer of GAG by the cross-linking agent remaining in the GAG structure and/or by the inherent crosslinking abilities of the charged moiety. Following the cross-linking of the charged molecule to the outer layer, the structures can be treated to remove the remaining crosslinker, e.g., by flushing the structure with an appropriate liquid. Alternatively, when the charged moiety has inherent cross-linking ability, the excess cross linking agent in the core of the GAG structure can be removed prior to resurfacing.

In either case, the crosslinked outer layers of the structure retain the free GAG within the core of the structure, while allowing the remaining crosslinking agent (e.g., glutaraldehyde and/or excess charged moiety) to be flushed from the structure. This removes any cross-linker than may have a potentially adverse effect in an in vivo atmosphere.

The crosslinked outer GAG layer and the crosslinked resurfacing layer both serve as a protective coating to the free GAG to prevent dissolving of the GAG structure upon contact with a liquid, e.g., a body fluid. The coating also allow cells access to the GAG, thus providing accessibility of GAG in a particular region for desired period, from a matter of hours or days, up to 3–6 months, and even up to a year or years in an appropriate environment. The resurfaced outer layer of charged molecule further provides a surface that promotes cellular attachment, thus allowing cells to access the free GAG present in the GAG structure.

The form of the GAG structure can be controlled by the shape of the GAG substrate subjected to crosslinking. For example, when strands are desired, the GAG solution can be produced as a stream, either into a liquid or onto a solid surface for subsequent drying of the GAG solution. The GAG solution stream can be introduced in any manner that can produce an elongated cylindrical shape, such as with a syringe. The structures can be as short as 10 microns, and as long as a meter, although generally the structures are between 0.5 and 5 cm, and more usually between 1.5 to 2.5 cm in length. The diameter of the strands can be determined by the diameter of the introduced stream, e.g., by a specific gauge of a needle used to introduce the GAG solution into the liquid. In another example, when spherical structures are desired, the GAG solution can be introduced as drops, with the diameter of the drop determining the diameter of the GAG structure. Following production of the GAG structures, the GAG structures are optionally dried prior to further processing.

In addition to individual GAG strand, the GAG structures may take another form, e.g., a sponge, gauze, spray or gel. These forms may be predetermined by the GAG substrate, or the form may be determined by coating a pre-existing structure (e.g., a sponge or gauze) with GAG. In addition, the GAG substrate may be molded prior to crosslinking, either before or after the substrate drying stage.

The methods of the invention also allow the formation of a GAG structure on a surface. This allows a surface to have a coating of free GAG with an exterior coating of cross-linked GAG, which is useful for coating surfaces such as sutures or bandages. This allows the surfaces to retain the GAG, since it will not immediately dissolve upon contact with a bodily fluid.

In a particular embodiment of the invention, the resurfaced GAG structures are composed of hyaluronan (HyA). HyA is a repeating disaccharide of $[GlcNAc\beta 1\text{-}4GlcUA\beta 1\text{-}3]_n$ that exists in vivo as a high molecular weight linear polysaccharide. HyA is found in mammals predominantly in connective tissues, skin, cartilage, and in synovial fluid, and is also the main constituent of the vitreous of the eye. In connective tissue, the water of hydration associated with HyA creates spaces between tissues, thus creating an environment conducive to cell movement and proliferation.

HyA plays a key role in biological phenomena associated with cell motility including rapid development, regeneration, repair, embryogenesis, embryological development, wound healing, angiogenesis, immune response and tumorigenesis (Toole, *Cell Bioi. Extracell. Matrix*, Hay (ed), Plenum Press, New York, 1384–1386 (1991); Bertrand et al. *Int.* J: *Cancer* 52:1–6 i (1992); Knudson et al, *FASEBJ:* 7:1233–1241 (1993>>. The HyA structures of the invention can be used to modulate any of the processes which involve HyA. For example, increased binding of HyA to one of its receptors, CD44, has been shown to mediate the primary adhesion ("rolling") of lymphocytes to vascular endothelial cells under conditions of physiologic shear stress, and this interaction mediates activated T cell extravasation into an inflamed site in vivo in mice. H. C. DeGrendele, et aI., J: *Exp. Med.* 183:1119–1130 (1996); H. D. DeGrendele, et al., *Science* 278:672–675 (1997). H. C. DeGrendele et al., J: *Immunol.* 159:2549–2553 (1997).

In another embodiment, the GAG structures are formed from two or more different GAGs, e.g., an HyA-heparinstructure. These heterologous GAG structures can comprise two or more different GAGs on the structure surface, within the structure as free GAGs, or both. Such heterologous GAG structures can be used where it would be advantageous to have multiple GAGs in the structure, e.g., to modulate a biological function involving multiple GAGs. For example, as discussed above, HyA is involved in immune responses, and particularly in leukocyte rolling. Heparin is also involved with leukocyte rolling, adhesion, and migration (Salas A et al. *Gut* 47:88–96 (2000)), and thus a structure having both HyA and heparin can be especially useful to modulate such processes.

In another embodiment, the GAG structures can be cultured with cells of interest (e.g., fibroblasts, keratinocytes, endothelial cells, macrophages and/or epithelial cells) and the cultured GAG structures can be used either externally (e.g., in a liquid bandage) or internally (e.g., to enhance healing of an vein or artery). Preferably, the cells that are incubated with a GAG structure are autologous to the subject to be treated with the GAG structure. For instance, when a GAG structure is to be used as a liquid bandage for a specific subject, the cells from an initial cleaning of the wound can be incubated with the GAG structure prior to application of the liquid bandage. The liquid bandage containing such autologous cells can speed the healing process by facilitating the restructuring of the wound situ without prompting an immune response due to foreign cells. In another example, where a wound to be treated is a wound from which it is difficult to obtain viable cells (e.g., a burn), the cells may be taken from another region in the individual to be treated. The GAG structures can also be incubated with cultured cells or cells obtained from other sources (e.g., another subject).

Methods of Treatment Using the Resurfaced GAG Structures of the Invention

The GAG structures of the invention can be used in any environment that it would be desirable to have a stable composition of a GAG and/or for delivery of free GAGs. This includes use of the GAGs in internal regions, such as introduction of the GAG devices into the synovial fluid of a joint, and the use of GAGs in an external fashion, such as application of these delivery devices to a wound. The following described methods of treatment are exemplary to illustrate both internal and external uses of the delivery devices of the invention. Other potential methods of treatment and uses of the resurfaced GAG structures will be apparent to one skilled in the art upon reading this disclosure, and the invention is intended to cover such additional treatments and uses.

Internal Introduction of the GAG devices of the Invention to Treat Arthritis

High-molecular-weight HyA produced by the synovium may function physiologically to aid preservation of cartilage structure and prevent arthritic pain; both the size and concentration of HyA in synovial fluid are diminished in osteoarthritis (OA).

HyA and albumin act together at normal concentrations to conserve synovial fluid in the presence of raised drainage pressures. Hyaluronan has the greater effect, acting osmotically by way of a concentration polarization boundary layer. Attenuation of this effect in arthritic effusions with low HyA concentrations is one of several factors limiting fluid accumulation and, hence, the size of the effusion. See, e.g., Scott D et al., *Arthritis Rheum* 43:1175–82 (2000).

In addition, certain sulfated GAGs and polysaccharides—including chondroitin sulfate (CS), dermatan sulfate, and pentosan polysulfate—stimulate synovial HyA production, apparently owing to a hormone-like effect triggered by the binding of these polymers to membrane proteins of synovial cells. See, e.g., McCarty M F et al., *Cancer Treat Rev* 54:798–802 (2000). The galactosamine-containing sulfated GAGs have a specific stimulatory effect on HyA synthesis in the synovial membrane. See, e.g., Nishikawa H et al., *Arch Biochem Biophys* 240:146–53 (1985). A high degree of sulfation of the molecules appeared to potentiate the stimulatory effect.

The GAG structures of the present invention can be used to retain synovial fluid in the joints of an individual. The structures may be composed of HyA, other GAGs that stimulate HyA production, or a combination of these. The HyA structures can be used to directly administer the HyA into a region to conserve the synovial fluid of a particular region, e.g, by direct administration of a resurfaced HyA structure into the joint via injection. Structures having GAGs such as chondroitin sulfate can also be administeredd directly into the joint to stimulate HyA synthesis by synovial cells. In addition, each of these GAG structures can be cultured with cells (e.g., synovial cells) prior to introduction of the GAG structures into the joint.

An effective amount of a GAG structure to be administered to a subject to obtain a desired physiological effect, e.g., retention or production of synovial fluid, can be determined by the caregiver in each case on the basis of factors normally considered by one skilled in the art to determine appropriate dosages, including the age, sex, and weight of the subject to be treated, the condition being treated, and the severity of the condition being treated.

Internal Administration of GAG Structures for the Maintenance of Internal Tissues The administration of certain therapeutics, such as glucocorticoid administration, can induce atrophy of skin, bone, and other organs, partly by reducing tissue content of GAGs, and in particular by reduction in HyA. For example, glucocorticoids induce a near-total suppression of hyaluronan synthase mRNA in dermal fibroblasts and in osteoblasts, a molecular mechanism contributing to effects such as organ atrophy. (Zhang W. et al. *Biochem J*349:91–97 (2000)). These effects can be counteracted by administration of GAG structures of the invention in a manner that will allow the delivery of the desired GAG to a particular organ. This can be accomplished by, for example, oral administration, intravenous administration, parenteral administration, the implantation of a drug delivery device that would deliver the GAG structures to a particular organ, and/or a patch that can be applied to an organ, e.g., a patch either coated with the free GAG having an outer layer of crosslinked GAG or comprising GAG structures that allow introduction of the GAGs into the tissue. The dosage used can be determined based on the method of administration as well as on the basis of other factors normally considered by one skilled in the art, e.g., the age, sex, arid weight of the subject to be treated.

Internal Administration of GAG structures to Prevent Arterial Restenosis

The GAG structures of the present invention can also be used to stimulate growth of endothelial cells to prevent the narrowing of vascular tubular walls by the proliferation of the endothelial cells on the area of trauma. For example, arteries which have been subjected to balloon angioplasty can be treated with the GAG structures of the invention, and in particular with HyA structures before, during or after the balloon angioplasty. Methods for such administration are disclosed in, for example, U.S. Pat. No. 6,022,866 issued to Falk et al. on Feb. 8, 2000.

External Administration of Resurfaced GAG Structures to Promote Wound Healing

The GAG structures can also be used externally to promote healing of external wounds (e.g., lacerations, surgical incisions, ulcers, ocular lesions, and bums) by providing the GAG structures to the external site of the wound. The GAG structures as described herein can be administered to the wound using a variety of different delivery devices.

Solid Wound Dressings

In one embodiment, the GAG structures of the invention are administered to the wound site via solid substrates comprising and/or coated with GAG structures. These solid substrates are intended for use as a temporary dressing on the burns, wounds and other lesions. The dressing itself forms a barrier against bacterial or other contamination, and the inherent antimicrobial properties of the HA provide a chemical means for maintaining sterility. The dressing preferably remains flexible and facilitates movement. The GAG structures may be impregnated into the dressing, or may be coated on the dressing, with the coating on the side to lie adjacent to the patient. Types of wound care dressings encompassed by the invention include, but are not limited to, alginates, composites, exudate absorbers, foams, gauzes, hydrocolloids, and hydrogels. Exemplary bandages for use with the present invention include, but are not limited to, those described in, for example, U.S. Pat. Nos. 5,718,674, 5,692,937, 5,499,966, 5,376,067, 4,867,821, 4,672,956, 4,655,202 and 4,377,159. For a review, see e.g., Bulpitt P and Aeschlimann D. *J BiomedMater Res* (1999) 47:152–169.

The dressing of the invention may be formed from any material known in the art, including biologically derived materials and synthetic materials. Generally, the flexible solid substrate is a synthetic material, and more preferably a woven synthetic material in the form of a mesh. In an exemplary embodiment, the flexible substrate is a multifilament or monofilament polyester mesh sheet. In another example, a sponge or other substrate may replace the mesh netting, where medically appropriate and if its properties match the desired end. The coated free GAGs are applied to the substrate of the dressing, e.g., a fibrous mesh netting, as an aqueous solution and dehydrated.

The dressing may be used directly, or may be adhered to a backing, e.g., a self-adhesive backing. Such backing is generally of a flexible material, and usually has an adhesive on the backing surrounding the dressing to allow self-adhesion of the bandage. In one example, the backing is a flexible strip having a coating of adhesive deposited on at least the lower planar surface of the strip. A dressing pad of the invention is attached to, for example, the lower planar surface of the strip and centered such that a portion of the adhesive strip extends from each end of the wound pad. The wound pad and strip are die cut in a predetermined shape, thereby separating the wound pad and strip into an outer surrounding frame and inner bandage. Exemplary bandages are described in, for example, U.S. Pat. Nos. 5,792,092 and 5,685,833, which are incorporated herein by reference.

The dressing of the invention can also be separate and held in place by the elastic forces of a bandage, e.g., a gauze coated with coated free GAGs held in place by an elastic bandage. Elastic bandages for use in the invention preferably have good elastic properties, which can be uniform over the width of the bandage. The fabric may be woven or preferably non-woven. The use of a non-woven fabric in elastic bandages of the invention can provide a desirable textile 'feel' to the surface of the bandage. Additionally use of an absorbent non-woven fabric can provide the bandage with a degree of absorbency for water and body fluids such as blood. In one example, an elastic bandage can be used which comprises an inner layer of fabric and an outer layer of fabric bonded to a central layer, such as is described in, for example, U.S. Pat. No. 4,414,970.

A vapor permeable film of plastic material may additionally be joined to one side of the impregnated mesh netting to form an external surface of the dressing. The cast dressing is then cut to the desired size of individual dressings.

The GAG delivery compounds of the invention may be added in an amount that allows effective dissemination of the GAG activity from the adhesive preparation. In one embodiment, the GAG structures are coated onto the bandage using a solution containing from about 0.5% to about 20% of the resurfaced GAG structures.

Liquid Bandages

In yet another embodiment of the invention, the GAG structures can be administered to a wound in the form of a liquid bandage. By "liquid bandage" is meant a flowable substance that can be administered onto or into a wound that aids in the closure and/or healing of the wound. Liquid bandages can include chemical or biological wound sealants, structural elements that serve as scaffolding for the reconstruction of the epithelium, compounds that prevent infection or alleviate pain, an the like. Liquid bandages of the present invention comprise GAG structures, and in particular GAG structures composed of HyA. In a particular embodiment, the GAG structures are cultured with a subject's autologous cells (e.g., fibroblasts) before administration.

One example of a wound sealant is fibrin sealant, which is comprised of fibrinogen and a fibrinogen activator such as thrombin and batroxobin. The fibrinogen activator can be present in various concentrations depending on the desired time to form a clot. When the fibrinogen activator is thrombin, at thrombin concentrations greater than 100 units per ml or so in the wound sealant, the fibrinogen concentration becomes the rate limiting step in coagulation. At concentrations lower than about 100 $\mu$/ml, the thrombin level is the rate controlling substance in the wound sealant. Thus, thrombin concentration can be used to control the time to gelation.

Another example of a wound sealant is a platelet glue wound sealant comprising a plasma-buffy coat concentrate as described in, for example, U.S. Pat No. 5,733,545. This sealant contains platelets, fibrinogen, and a fibrinogen activator in a concentration sufficient to initiate clot formation.

The GAG structures of the invention may be added in an amount to effectively treat and/or prevent infection in a wound. Generally, the GAG structures are used in the liquid bandage in a concentration of from about 0.5 to 40%, usually from about 1.0 to 20%, more usually between from about 5 to 10%.

Liquid bandages can be used alone or with additional help from other closing devices or methods. For example, liquid bandages can be used in conjunction with sutures, adhesive tape, bandages, and the like to improve wound closure integrity. Liquid bandages can also be used alone, e.g., in situations involving coagulopathy, friable tissues, adhesions that cause bleeding when sutures would be ineffective to control the bleeding, and the like. Other potential uses of liquid bandages of the invention include sealing vascular suture lines, reinforcing pulmonary and esophageal staple lines and fixing split-thickness skin grafts. See, e.g., Spotnitz et at., *Wound Heating*, 77:651–669 (1997).

Sutures

Sutures are often used in the closing of a wound, and currently suturing is the method of choice for closing most surgical wounds. The type of suture used will vary depending on the type and extent of the wound, the tissue involved, and a particular patient's healing ability. The GAG structures of the invention may be used to coat the sutures in an amount that allows effective activity from the coating. Generally, the concentration of GAG structure in solution is used in a concentration of from about 0.5 to 40%, generally from about 1.0 to 20%, usually between about 5% to 10%. The sutures may also be directly coated with GAG, with free GAG surrounding the suture and a crosslinked GAG layer surrounding the free GAG. The sutures are preferably coated with a resurfacing molecule.

Sutures within the scope of this invention can be of any type used or contemplated for use in wound closure. The suture can be synthetic or natural, absorbable or nonabsorbable, or a monofilament or multifilament in a braided, twisted or covered form. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from fiber-forming polymers of one or more lactones, e.g., Vicryl.RTM. poly(lactide-co-glycolide) multifilament suture. Examples of non absorbable monofilament and multifilament sutures include nylon, polypropylene, steel, polyvinylidene fluoride, linen, cotton, silk, and polyesters such as polyethylene terephthalate (PET). In one embodiment the sutures are nonabsorbable, multifilament sutures, generally polyester sutures, e.g., PET.

Adhesives

The present invention also includes an adhesive compound which incorporates an adhesive component comprising a GAG structure. The GAG structures can be homogeneously dispersed throughout the adhesive layer. Active GAG structures of the present composition disassociate from the surface or allow the GAG activity to be adminis- 
tered over time, delivering healing activity at a distance from the adhesive surface.

The adhesive of the present invention is specifically suited for use in skin contact applications during and after medical procedures, for example, as an adhesive in surgical drapes, wound dressings and tapes. A particular adhesive composition incorporates acrylic polymers and added tackifiers to form an adhesive which is particularly suited for use in medical procedures.

An exemplary combination of acrylic polymers to form the adhesive composition includes the combination of a low molecular weight solid acrylic polymer and a medium molecular weight solid acrylic polymer in a ratio of about 1 to 4, respectively, to optimize the adhesion of the adhesive to skin, cohesion and resistance to cold flow. A low molecular acrylic polymer is a polymer having a molecular weight ranging from about 90,000 to about 120,000, while a medium molecular weight acrylic polymer has a molecular weight ranging from about 140,000 to about 160,000. Suitable low molecular weight solid acrylic polymers and medium molecular weight solid acrylic polymers are available from Schenectady International, Inc. under Product Nos. HRJ-4326 and HRJ-10127, respectively.

The adhesive component of the composition can also include tackifiers as are well known in the art. Tackifiers contemplated include SYLVATEC, ZONAREZ and FORAL which are available from Arizona Chemical and Hercules, Inc.

The coated free GAGs of the invention may be added in an amount that allows effective dissemination of the activity from the adhesive preparation. Generally, the coated free GAG is used in a concentration of generally from about 0.5 to 40%, usually from between about 1.0 to 20%, more usually from between about 5 to 10%.

Skin Substitutes

Another embodiment of the invention provides skin substitutes that coated with free GAG having an outer layer of cross-linked GAG and/or comprise coated free GAGs. Skin substitutes are commonly used as dressings, especially for burn victims. They can be used to maintain a clean wound environment until skin grafting can be achieved, or may be a dressing placed on a partial-thickness wound. The GAG structures can either be bound to the surface designed to be adjacent to the patient, or interspersed throughout the skin substitute. For a review of such skin substitutes, see, e.g., Staley et al., *Adv. Wound Care* 10:39–44 (1997).

In one embodiment, the skin substitutes of the invention are biosynthetic dressings. These include: Biobrane, a flexible nylon fabric impregnated with collagen and bonded to a silicone membrane; collagen derivatives such as SkinTemp™, Medifil™, Kollagen™, which are typically formed from animal collagen; EZ-Derm™, a pigskin impregnated with the preservative aldehyde; and alginates, which are derived from seaweed and release calcium ions to help with homeostasis. These dressings may be coated with the GAG structures of the invention and/or have the GAG structures impregnated into the fiber of the dressing.

Cultured skin substitutes can also be used in the present invention. These include, but are not necessarily limited to: cultured epidermal autografts, which are produced from a patient's own keratinocytes; Dermagraft, having a collagen base with human neonatal fibroblasts injected into the matrix; Composite skin, a bilayered cultured skin containing human fibroblasts on a bovine collagen lattice; Alloderm™, an allograft dermis with all immune cells removed; and Integra™, a bovine collagen dermis with an outer silicone membrane layer. These skin substitutes can be coated with GAG structures of the present invention to help promote healing of the area treated with the skin substitute. Other similar skin substitutes can also be used, as will be apparent to one skilled in the art upon reading this disclosure. The skin substitute may be impregnated with the GAG structures, or it may be coated on the side that will contact the patient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for: Unless indicated otherwise, parts are parts by weight, molecular weight is weight average molecular weight, temperature is in degrees Centigrade, and pressure is at or near atmospheric.

Example 1

Production of Hyaluronan Strands

First, to prepare the HyA solution for the cross-linking reaction, the commercially available compound sodium hyaluronate (MW 1.6×106 Daltons; Lifecore Biomedical Inc.) was subjected to a cation exchange reaction. Samples of 0.15 g HyA were put into autoclaved dialysis tubing and dialyzed against cation exchange cellulose (Dowex AG 50W-X4, from BIO-RAD) at 19/100 ml of deionized distilled water and stirred by a magnetic bar at 4° C. for 2 days. The samples were rinsed with sterile water, and liquefied HyA was transferred into DMSO. After 2 days of further stirring, HyA was aspirated into 10-ml syringes.

The HyA solution in the 10 ml syringes was then used to prepare strands of HyA. The prepared HyA was pushed out of the 10-ml syringes through a 25-gauge (0.5 mm) needle to form strands in a beaker filled with 100% alcohol with 10% dimethyl sulfoxide (DMSO) and stored at 4° C. overnight. The strands were placed on 5-mm filter paper and air dried. Then samples in the experimental group were immersed in biological grade glutaraldehyde (TED PELLA, Inc.) at concentrations of 0.5, 5, 25, and 50% aqueous solution for 1, 2, 4, 6, 8, 12, 24, 48, or 72 h at 4° C. After extensive washing in distilled water, the strands were dialyzed in PBS for 48 h in order to reduce residual glutaraldehyde. The samples then were stored in PBS overnight.

Fabricated HyA strands crosslinked by 50% glutaraldehyde for 72 hours were water insoluble and very stable compared to the groups crosslinked with lower concentrations of glutaraldehyde or for shorter incubation times (Table 1). HyA strands, crosslinked for 72 hours or longer with 50% glutaraldehyde maintained their shape for at least 5 days to over 3 months (FIG. 1, 2), while the groups crosslinked by 50% glutaraldehyde for 48 hours would dissolve in PBS or distilled water after 2 days. When lower concentrations of glutaraldehyde were used, such as 25% glutaraldehyde, the strands dissolved in PBS in from 5 min to 12 hours while all other experimental groups crosslinked with concentrations of glutaraldehyde less than 25% immediately dissolved in PBS or distilled water.

Example 2

Resurfacing Crosslinked HyA Strands

The crosslinked HyA strands were then resurfaced to determine the ability of different surface to adhere to cells. Solutions of 1% L-glutamine (Sigma), 1% glycine (aminoacetic acid, BIO-RAD), 50 mg/1 mL of poly-L-lysine (Sigma), and 10 mg/ml of poly-D-lysine (Sigma) were freshly prepared. Sets of HyA strands crosslinked with 50% glutaraldehyde were immersed in one of four solutions for 1 hour, with an additional set receiving no resurfacing treatment. After immersion, the strands were washed thoroughly with distilled water.

The crosslinked, resurfaced HyA strands were then prepared for visualization of the external coating of the strands. The crosslinked, resurfaced HyA were impregnated in the tissue culture medium. The cultured HyA strands were then washed in PBS for 30 min, fixed in 10% neutral formaldehyde for 1 hour, and washed again in PBS for 30 min prior to staining. Strands were then incubated with Alcian Blue solution for 30 min, rinsed with PBS three times for five min, followed by rinsing with distilled water 3 times for 3 min. The strands were put on a glass slide and mounted with Gelatin. Photographs of intact, stained HyA strands at 400× magnification showed that the resurfaced crosslinked HyA strands have a distinct structure, with a light green-blue color outlayer of the crosslinked HyA strands.

Figure 1:
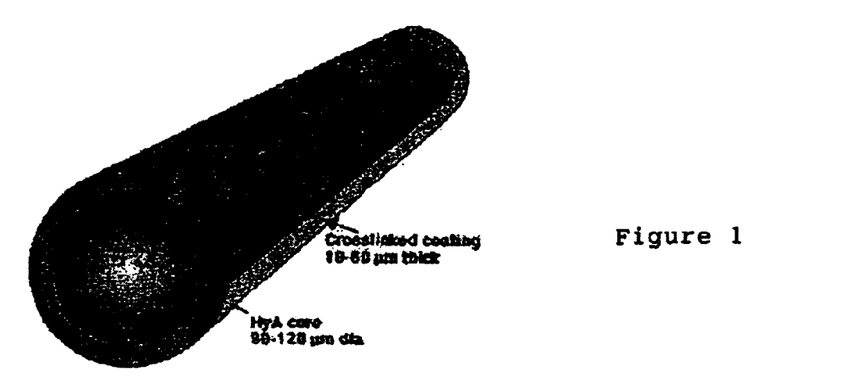
FIG. 1 is a figure of the modified HyA strand that shows the natural HyA core with a modified outside layer.
Figure 2:
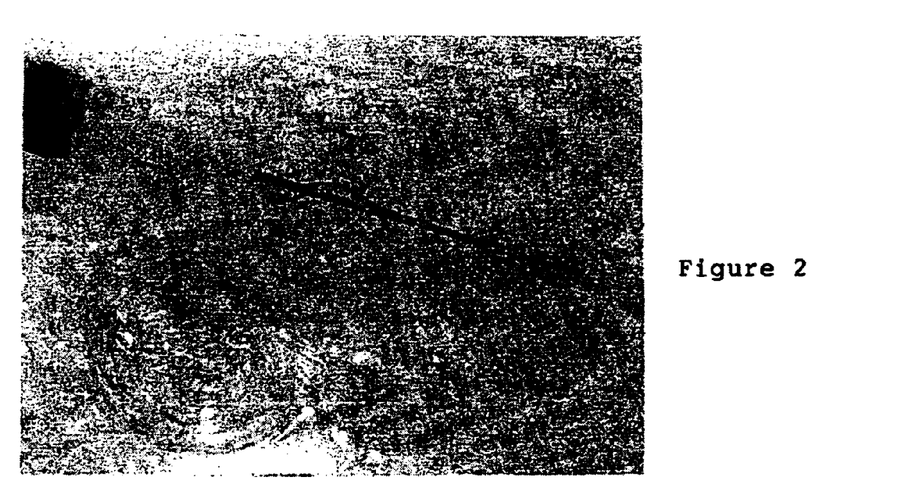
FIG. 2 is a photograph demonstrating that the fabricated HyA strand is transparent, soft and conformable to fit into many kinds of wounds.
Figure 3A:
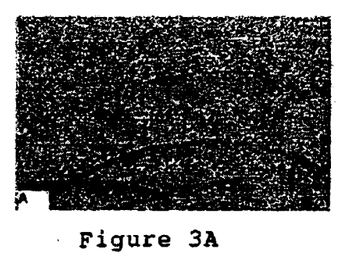
FIGS. 3A, 3B, 3C, and 3D are photographs indicating the function of the surface modification by polylysine. A. Cells are sliding away from the HyA strands without polylysine treatment. B. After the surface has been treated by polylysine, The HyA strand becomes not cell repellant. C. Fibroblasts are growing on the HyA strand. D. PCNA positively staining shows that the cell's proliferation is enhanced.
Figure 3B:
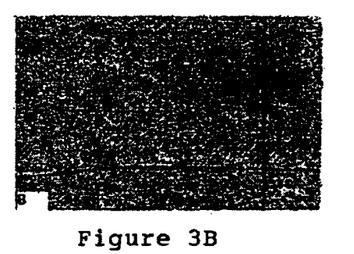
Figure 3C:
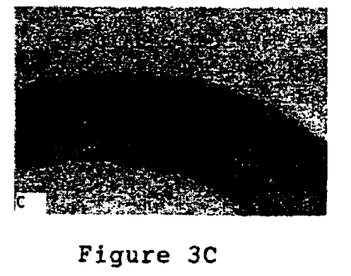
Figure 3D:
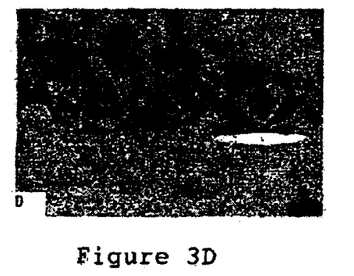
Figure 4A:
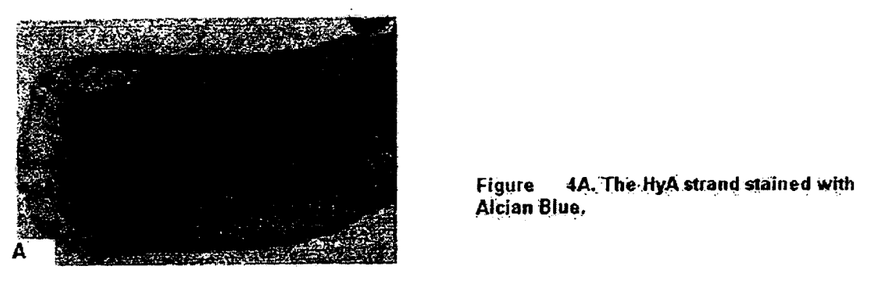
FIGS. 4A, 4B, and 4C are photographs showing an intact stained resurfaced HyA structure. A. The photograph showing a stained resurfaced HyA intact structure, B. In this HyA strand, the outer core has been smashed to reveal the inner core of free HyA, C. A photograph illustrating the ability of fibroblasts to access the core of free HyA in a resurfaced HyA structure
Figure 4B:
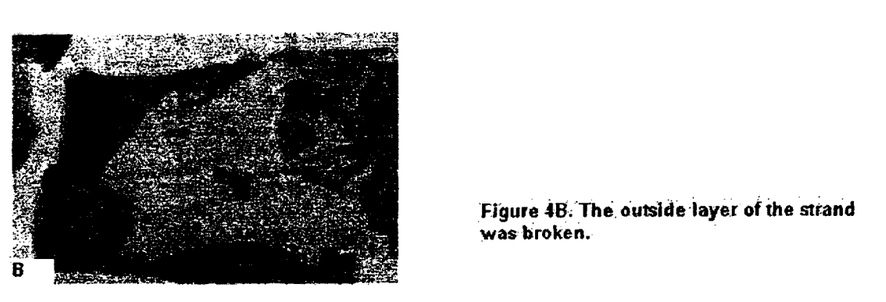
Figure 4C:
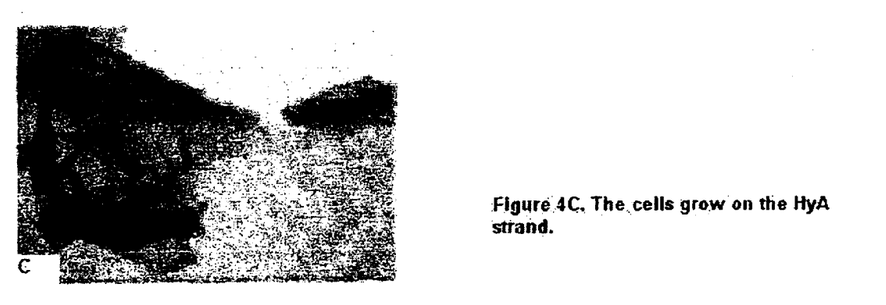
Figure 5A:
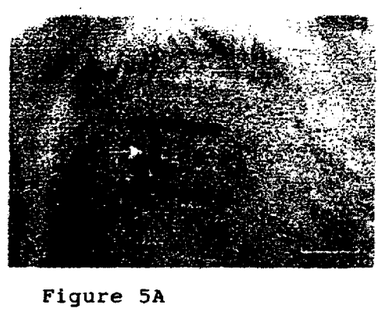
FIGS. 5A, 5B, 5C, and 5D are photographs illustrating HyA graft implantation into the rat. A. Full thickness incisions were made on the rat's dorsal upper back. Left side wound was treated with HyA strands, right side with only saline washed. B. Three days after the surgery. HyA strand treated wound healed without contraction. While the right side wound was still open, bled and contracted. C. Five days post-surgery. The left wound healed with a clear fine line. The right side wound healed with blood clot and contraction. D. Ten days after surgery. The left side wound fully healed with merely visible line. The control side (right) wound showed a typical contracture as a usual healing result.
Figure 5B:
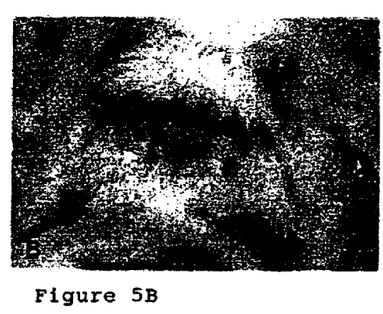
Figure 5C:
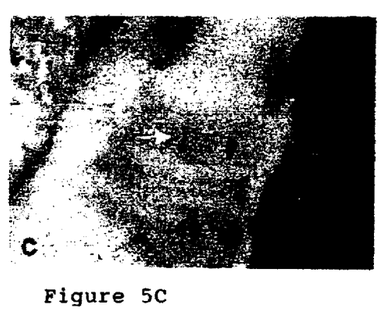
Figure 5D:
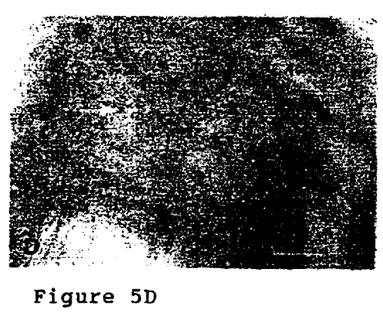

The stained crosslinked HyA strands were then put through a series of alcohol baths increasing in concentration from 70% to 100% alcohol. The strands were kept in 100% alcohol for 0.5 hours, changing the alcohol three times, to make the surface of the strands tough and rigid. Then the surface of the strands were cracked with a glass cover slip to reveal the internal core of the strands. The stained outer layers display crosslinking only at the periphery of the strand, with an internal core of unstained, free HyA (FIGS. 4A–4C).

Example 3

Fibroblast Growth on Resurfaced HyA Strands

Each of the 4 different sets of resurfaced HyA strands were tested for their ability to provide bioactive HyA to cells. Monolayers of rat fibroblasts in their growth phase, approximately 3 days after splitting, were trypsinized for 15 min to form a suspension. Cells were pooled by centrifugation at 2000 rpm for 10 min and resuspended in DMEM, 4–6×10$^5$/cm$^2$. A syringe with a cut-tip needle was used to aspirate and push out the cellular medium three to five times to homogenize the clumps of cells. Following homogenization, the fibroblasts were gently applied to the surface of the HyA strands in 35×10-mm culture dishes. 1 ml of medium (DMEM+10% fetal bovine serum) was added to each of the culture dishes. The cultures of cell-seeded HyA strands were incubated at 37° C. and observed at 24 h intervals for 7 days using an inverted microscope. The culture dishes were then washed in PBS for 30 min, fixed in 10% neutral formaldehyde for 1 hour, and washed again in PBS for 30 min prior to staining (FIGS. 3A–3D).

Specimens were incubated in 0.3% H$_2$O$_2$ for 30 min, washed in PBS, and blocked with normal horse serum for 30 min. Following blocking, the specimens were incubated overnight with PCNA antibody (mouse anti-proliferative cell nuclear antigen, pc-10, DAKO) at 1:200 dilution. Afterwards specimens were treated with the avidin-biotin-complex kit (Vector), developed with DAB tablets (Sigma), and mounted with gelatin. Other specimens routinely were stained with H&E or Alcian Blue. A Baxter cell counter was used to count cells attached to a 1-cm segment of a HyA strand. Proliferating cells were marked by PCNA-positive staining. The proportion of positively stained cells was assessed and graded on a scale of 0 to ++++ (0=negative immunoreactivity; +=1–25 percent; ++=26–50 percent; +++=51–75 percent, and ++++=76–100 percent).

Although 50% Glut-crosslinked HyA strands dimensionally were stable in culture medium, there was no attachment of fibroblasts following inoculation with the non-resurfaced HyA strands. After resurfacing with polylysines, the adhesive ability of the HyA strand surface was enhanced, especially with poly-D-lysine, whereas L-glutamine and glycine coating did not facilitate cell attachment. Poly-D-lysine improved adhesion most effectively, attaching 50–100 cells per centimeter of HyA strand, and poly-L-lysine was effective to a lesser extent, attaching 40–80 cells per centimeter. The results are summarized in Table 1:

TABLE 1

Adhesion and Proliferation of Fibroblasts on HyA Strands Resurfaced With One of Four Different Amino Acids or Polypeptides

| Resurfacing Treatment | Cell Attachment Count Proliferation (Average # per 1 mm HyA Strand) | Proliferation |
|---|---|---|
| None | 0–2 | – |
| Poly-D-lysine | 50–100* | ++ |
| Poly-L-lysine | 40–80* | ++ |
| Glycine | 0–7 | + |
| L-glutamine | 0–5 | + |

*$p < 0.01$.

Also, both polylysines allowed cell growth on the surface of the HyA strands for at least 1 month. Fibroblasts on the strands stained positively for PCNA but not as strongly as for those that grew beside the strands on the bottom of the culture dish. Cells adhering to the polylysine-coated strands showed more proliferation (26–50% PCNA immunostaining) than cells on the other treatment. PCNA mainly was localized to cell nuclei, but some staining also was scattered in the cytoplasm.

Biocompatibility of the resurfaced glutaraldehyde-crosslinked with fibroblasts was demonstrated using the cell-seeded HyA strands. The fibroblasts grew in vitro without inhibition or toxicity along and over the HyA material as well as on the dish bottom. Visualization of the interaction of the cells with the HyA strands was achieved using the Alcian Blue staining protocol as described in Example 2. The fibroblasts on the HyA strand have been shown to extend into the core region of the strand, where the free HyA is contained, and therefore allows the cells access to the free HyA (FIGS. 4A–C).

Example 4

Inoculation with HyA Strands in vivo

Each of the 4 different sets of resurfaced HyA strands were also tested for their ability to provide bioactive HyA following in vivo implantation. Five Wistar male rats weighing about 400 g were anesthetized with intraperitoneal injections of 4% chloral hydrate. Four segments (of 2 cm each) of the fibroblast-seeded HyA strands were implanted in a subcutaneous pocket in the right chest of the rat, and the incision was closed with a continuous 4.0 nylon suture.

After 2 or 4 weeks the rats were sacrificed, the implants with surrounding tissue were removed, and the specimens were fixed in buffered formaldehyde for 2 hours. The specimens were processed, paraffin embedded, and cut into 10 mm sections onto slides. The slides then were deparaffinized and rehydrated in preparation for staining.

In vivo, implantation for 4 weeks in rats did not elicit any apparent inflammatory or necrotic response. Under microscopic examination, HyA strands maintained their shape and cells grew along the strands. PCNA staining of implanted strands showed activity proliferating cells, graded at "++", on strands resurfaced with poly-L-lysine and poly-D-lysine. Surrounding connective tissue infiltrated the space around the implant, but few inflammatory cells, macrophages, or lymphoid cells migrated to the area.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 5

Wound Treatment with HyA Strands

Thirty male or female SD rats weighing 400 grams were fully anesthetized. Two parallel full-thickness incisions 1.5 cm in length were made 2 cm apart from each other on the dorsal skin of their upper back. HA strands with or without cultured cells, both 6 cm long, were immediately inserted into the acute full-thickness bed in one of two wounds on each rat. The contralateral wounds received only saline wash but otherwise were processed identically, without suturing to approximate wound edges.

Five rats were sacrificed at the time points: 1day, 3 days, 7 days, 2 weeks, 4 weeks and 8 weeks post-surgery. The wound regions with the surrounding tissues were excised and fixed in 10% buffered formaldehyde and routinely processed, paraffin embedded, and cut into 5 micron sections perpendicular to the skin surface and transverse to the wounds. Half the tissue slides were stained with routine hematoxylin and eosin (H&E) and Alcian Blue. Immunohistological staining and the quantitative evaluation of the HA and HA+cell graft were performed as above described in EXAMPLE 3.

The wound closure time required for the experimental and control groups are shown in TABLE 2. Wounds treated with HA grafts or HA+cell grafts closed in 15.85±4.77 and 16.15±4.66 hours respectively. There was no significant difference between these two treatment groups (p>0.5). In contrast to the HA grafts, the controls had an average of 114.2±18.41 hours for the final closure of the wound which is significantly different (P<0.01) compared to the experimental wounds. About half of the control wounds were still bleeding or had fresh clots in the center of the wounds after three days.

TABLE 3 demonstrates the comparative scar areas among the three wound treatments under microscopy. Because all tissue specimens were taken vertically from the centers of the linear incision wounds, the measured areas were as uniform as possible. The averages of the cross-sectional wound areas were: HA only graft $0.151$ $mm^2 \pm 0.035$, HA+cell $0.143$ $mm^2 \pm 0.036$ and controls $14.434$ $mm^2 \pm 1.175$. There was less fibroblast proliferation, and almost no inflammatory cell infiltration in the experimental skin tissues compared to the tissue from the control group.

Figure 6A:
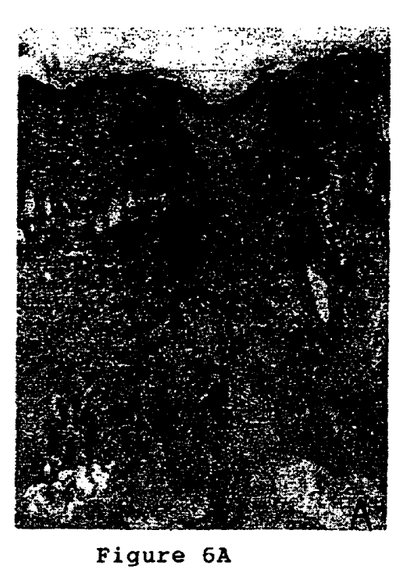
FIGS. 6A and 6B are photographs indicating the histologic morphology of the ten day's wound recovery area. A: the left side wound treated with modified HyA graft healed with less scar and few inflammatory cells infiltration. B. the right side control wound without the treatment had a much large area of scar with fibroblasts proliferation and inflammatory cells infiltration.
Figure 6B:
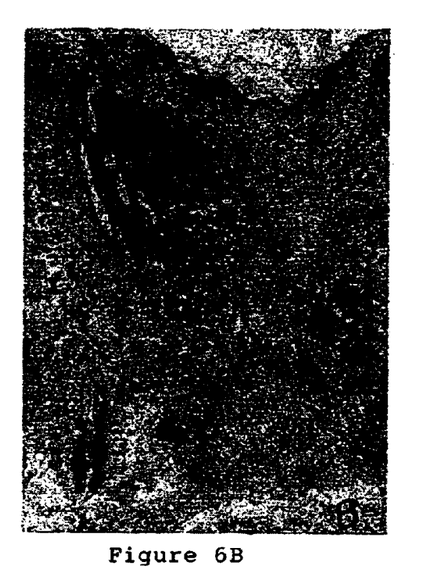

FIGS. 5(A–D) illustrates gross incision wound healing after HA grafts were placed into wounds. There was a dramatic difference in the closure rate between HA graft wounds and control wounds. Most HA only or H+cell treated wounds closed rapidly in a fine line without contracture. Some showed even faster closure: one hour after the graft was implanted, bleeding stopped and the wounds were closed. Afterwards, there was no bleeding when the rats moved. Microscopically, cutaneous appendages (including hair follicles, sweat glands and sebaceous glands) were found in the corresponding healing area. Compared to the experimental wounds, contralateral control wounds required longer time to achieve closure. These wounds demonstrated the routine course of non-sutured wound contracture, being contracted into bumps. Microscopically, the larger scar area of the controls contained more eosin stained disorganized matrix (collagen fiber bundles) with increased fibroblast and inflammatory cell numbers and increased vascularity. Fewer skin appendages could be seen in the healing area (FIGS. 6A and 6B).

That which is claimed is:

1. A method of promoting wound healing in a subject, said method comprising administering to said subject a composition comprising:

a multiple-layered glycosaminoglycan structure, wherein said glycosaminoglycan structure comprises a core of free glycosaminoglycan, a layer of crosslinked glycosaminoglycan strands surrounding said core;

a charged molecule surrounding said layer of crosslinked glycosaminoglycan strands; and an excipient.

2. A method for treating a glycosaminoglycan-mediated condition in a subject, said method comprising:

administering to said subject a composition comprising:

a multiple-layered glycosaminoglycan structure, wherein said glycosaminoglycan structure comprises a core of free glycosaminoglycan, a layer of crosslinked glycosaminoglycan strands surrounding said core;

a charged molecule surrounding said layer of crosslinked glycosaminoglycan strands; and an excipient.

* * * * *